United States Patent [19]

Rosenberger

[11] 4,076,690
[45] Feb. 28, 1978

[54] PHOSPHONATES, PROCESS FOR THEIR MANUFACTURE AND ORGANIC MATERIALS STABILIZED THEREWITH

[75] Inventor: Siegfried Rosenberger, Riehen, Switzerland

[73] Assignee: Ciba-Geigy Corporation, Ardsley, N.Y.

[21] Appl. No.: 663,953

[22] Filed: Mar. 4, 1976

[30] Foreign Application Priority Data

Mar. 10, 1975 Switzerland ..................... 3001/75

[51] Int. Cl.$^2$ ................................................ C08K 5/53
[52] U.S. Cl. .......................... 260/45.95 D; 252/48.4; 106/177; 260/953; 260/398.5
[58] Field of Search ............ 260/45.95 D, 986, 623 H, 260/488 CD, 953, 398.5; 106/177; 252/48.4

[56] References Cited

U.S. PATENT DOCUMENTS

| | | | |
|---|---|---|---|
| 2,603,662 | 7/1952 | Stevens et al. ................. | 260/623 H |
| 3,155,704 | 11/1964 | Knapp ......................... | 260/45.95 D |
| 3,367,870 | 2/1968 | Spivack ....................... | 260/45.95 D |
| 3,607,950 | 9/1971 | Platz et al. .................. | 260/623 H |
| 3,872,186 | 3/1975 | Fenyes et al. ................. | 260/45.95 D |

OTHER PUBLICATIONS

German Offenlegungschrift 2312910, Sep. 1974.
J.A.C.S. 75, 734–736(1953), pp. 734–736, Coppinger et al.
JACS–76:4977–4979 (1954) Forman et al.

*Primary Examiner*—V. P. Hoke
*Attorney, Agent, or Firm*—Nestor W. Shust

[57] ABSTRACT

3,5-Dialkyl-4-hydroxyphenylphosphonates or 3,5-dialkyl-4-hydroxyphenylalkylphosphonates are converted into the corresponding 3-halogeno-5-alkyl derivatives by means of a novel process by reacting them with a halogen or a halogenating agent. These compounds are outstanding stabilizers for protecting organic materials against degradation induced by heat and oxygen.

19 Claims, No Drawings

PHOSPHONATES, PROCESS FOR THEIR MANUFACTURE AND ORGANIC MATERIALS STABILIZED THEREWITH

The invention relates to 5-alkyl-4-hydroxyphenyl-phosphonates and 5-alkyl-4-hydroxyphenylalkylphosphonates, a process for their manufacture and to their use as stabilisers in organic materials to prevent a thermooxidative degradation.

Sterically hindered phenols have long been known as effective stabilisers for preventing the degradation of organic materials induced by heat and oxygen, in particular of polyolefins. As examples there may be mentioned 2,6-di-tert.-butyl-4-methyl-phenol or the 3,5-dialkyl-4-hydroxybenzylphosphonates described in U.S. Pat. No. 3,155,704. A disadvantage of many of these stabilisers is, however, that they can effect a discolouration of the substrate.

The present invention has for its object to provide stabilisers with which an effective protection against degradation induced by heat and oxygen is attained while at the same time preserving a good substrate color even under prolonged and severe stress, for example during the processing of polyolefins in the melt phase.

Accordingly there are provided phosphonates of the general formula I

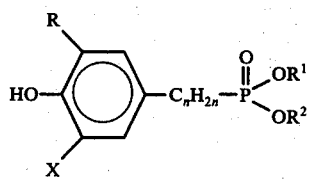

(I)

wherein

X represents a halogen atom,

R represents a linear or branched alkyl radical of 1 to 18 carbon atoms, a cycloalkyl radical of 5 to 8 carbon atoms or an aralkyl radical of 7 to 9 carbon atoms, $R^1$ represents an alkyl radical of 1 to 22 carbon atoms, a cycloalkyl radical of 5 to 7 carbon atoms, or phenyl or benzyl which is unsubstituted or substituted by alkyl, $R^2$ independently has the same meaning as $R^1$ or represents a hydrogen atom, and n is 0, or 1, 2 or 3.

Preferably, X in formula I represents a bromine and especially a chlorine atom, R represents an alkyl radical of 1 to 8, in particular 1 to 6, carbon atoms, of which in particular the α-carbon atom is branched, n is 0 or especially 1, and $R^1$ and $R^2$ represent an alkyl radical of 1 to 18 carbon atoms. Particularly preferred radicals R are those which possess a tertiary α-carbon atom.

Particularly useful phosphonates are those of formula I in which R represents an isopropyl or a tert. butyl group and X represents a chlorine atom. Preferred phosphonates of formula I are also those in which the alkyl radicals $R^1$ and $R^2$ are the same.

The radical R can be for example: methyl, ethyl, propyl, isopropyl, butyl, isobutyl, tert. butyl, pentyl, tert. amyl, hexyl, heptyl, octyl, tert. octyl, decyl, dodecyl, hexadecyl, octadecyl. The tert. butyl radical is particularly preferred. R can also be: cyclopentyl, cyclohexyl, α-methylcyclohexyl, cycloheptyl, cyclooctyl, benzyl, phenylethyl, 2-phenylpropyl.

The $C_nH_{2n}$ group in formula I can be linear or branched, and, if n is 1, 2 or 3, can represent the methylene, ethylene, propylene, ethylidene, 1- or 2-methylethylene or propylidene radical.

The alkyl radicals $R^1$ and $R^2$ can be linear or branched, but linear radicals are preferred. $R^1$ and/or $R^2$ can also be cyclopentyl, cyclohexyl, cycloheptyl, methylcyclohexyl, cyclohexylmethyl, alkylphenyl, for example methylphenyl to octadecylphenyl, benzyl, methylbenzyl, ethylbenzyl.

Examples of phosphonates of formula I are:
3-chloro-5-tert.-butyl-4-hydroxyphenyl-phosphonic acid-diethyl ester,
3-bromo-5-methyl-4-hydroxyphenyl-phosphonic acid-di-octyl ester,
3-chloro-5-tert.-octyl-4-hydroxyphenyl-phosphonic acid methyloctadecyl ester,
3-bromo-5-octadecyl-4-hydroxyphenyl-phosphonic acid dimethyl ester,
3-chloro-5-methyl-4-hydroxybenzyl-phosphonic acid decyl ester,
3-bromo-5-ethyl-4-hydroxybenzyl-phosphonic acid propylester,
3-chloro-5-isopropyl-4-hydroxybenzyl-phosphonic acid hexyl ester,
3-chloro-5-tert.-butyl-4-hydroxybenzyl-phosphonic acid diethyl ester,
3-chloro-5-tert.-butyl-4-hydroxybenzyl-phosphonic acid di-n-octadecyl ester,
3-bromo-5-methyl-4-hydroxybenzyl-phosphonic acid di-docosanyl ester,
3-chloro-5-tert.-pentyl-hydroxyphenylethylidene-phosphonic acid dibutyl ester,
3-bromo-5-hexyl-hydroxyphenyl-propylidene-phosphonic acid dipentyl ester,
2-(3'-chloro-5'-tert.-butyl-4'-hydroxyphenyl)-propyl-phosphonic acid diethylester.

The compounds of the present invention are obtained by means of a novel process by halogenating corresponding 4-hydroxy-3,5-dialkylphenyl- or -phenylalkyl-phosphonic acid dialkyl esters. The present invention therefore also provides a process for the manufacture of phosphonates of formula I

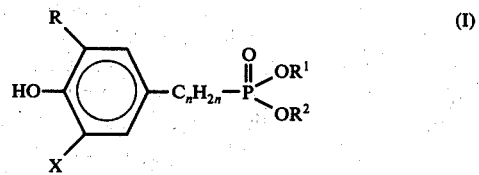

(I)

wherein

X represents a halogen atom,

R represents a linear or branched alkyl radical of 1 to 18 carbon atoms, a cycloalkyl radical of 5 to 8 carbon atoms, or an aralkyl radical of 7 to 9 carbon atoms, $R^1$ represents an alkyl radical of 1 to 22 carbon atoms, a cycloalkyl radical of 5 to 7 carbon atoms, or phenyl or benzyl which is unsubstituted or substituted by alkyl, $R^2$ independently has the same meaning as $R^1$ or represents a hydrogen atom, and n is 0 or 1, 2 or 3, which process comprises reacting a phosphonate of the formula II

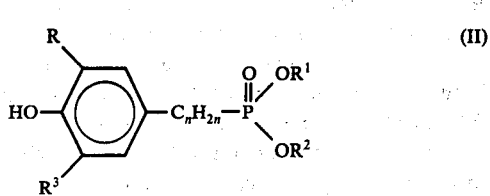 (II)

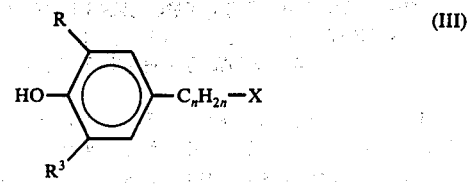 (III)

wherein R, R[1], R[2] and n are as defined in formula I and R[3] represents an alkyl or a cycloalkyl radical containing a tertiary α-carbon atom, in the presence of an inert solvent and optionally of a basic nitrogen compound, with a halogen or halogenating agent, and optionally subsequently hydrolysing the resultant diester to give the monoester.

Preferably R[3] is a tertiary alkyl radical of 4 to 8 carbon atoms, in particular tert. octyl or α-methylcyclohexyl and especially tertiary butyl.

The preferred temperature at which the process of the present invention is carried out is in the range from −20° to +30° C.

Suitable solvents for the process are, for example, halogenated hydrocarbons, including in particular low molecular compounds of alkanes, cycloalkanes, benzene or alkylated and/or halogenated derivatives thereof.

As examples there may be mentioned: pentane, cyclohexane, methylcyclohexane, chlorocyclohexane, methylene chloride, chloroform, carbon tetrachloride, chloroethane, 1,2-dichloroethane, difluorodichloroethane, dibromomethane, toluene, xylene, ethyl benzene, chlorobenzene or chlorotoluene.

Besides the halogens, such as bromine and, in particular, chlorine, examples of suitable halogenating agents are: thionyl chloride, sulphuryl chloride, phosphorus trichloride, phosphorus tribromide, phosphorus pentachloride, antimony pentafluoride, antimony pentachloride. Chlorine and sulphuryl chloride are preferred.

It has proved advantageous to use at least 1.5 moles of halogen or of a halogenating agent that yields 2 equivalents of halogen, per mole of phosphonate. If the halogenating agent yields 3 equivalents of halogen, then it is evident that 1 mole suffices to obtain a quantitative yield. It will be readily understood, however, that more than 1.5 moles or 1 mole can also be used.

Suitable basic nitrogen compounds are in particular amines, also cyclic amines. Tertiary amines, for example trimethylamine, triethylamine, pyridine, N-methylpyrrole, N-methylpyrrolidine, pyrazole, imidazole, N-methylpiperidine, N-ethylmorpholine, quinuclidine, are preferred.

Provided a corresponding monoester is not already used for the process of the present invention, the phosphonic acid monoesters of formula I (R[2] = hydrogen) can be obtained by partial hydrolysis after the diesters have been obtained. As a rule this reaction is carried out in water-miscible solvents, such as ethyl glycol, with alkaline earth hydroxides or alkyli hydroxides, for example sodium hydroxide.

The phosphonates of formula II are known compounds which are obtained by the Arbusov reaction by reacting trialkylphosphites containing 1 to 22 carbon atoms in the alkyl moiety with bromides or chlorides of the general formula III wherein R, R[2] and n are as defined as in formula II and X represents bromine or chlorine, with the simultaneous splitting off of 1 equivalent of alkyl chloride or bromide containing 1 to 22 carbon atoms in the molecule. By hydrolysing these diesters by the same methods as described hereinbefore it is possible to obtain monoesters, which are then used as starting products. High yields can be obtained with the process of this invention for manufacturing the compounds of formula I.

The compounds according to the invention of formula I are excellently suited to stabilising organic substrates against degradation induced by heat and oxygen. Surprisingly, they impart good stability to the substrate even when it is subjected to high temperatures over a prolonged period, for example during the processing of polymers in the molten state, without any material change in the good colour of the substrate. The compounds of this invention are also excellently suited to stabilising natural and synthetic fats and oils.

Examples of suitable substrates are:

1. Polymers, which are derived from singly or doubly unsaturated hydrocarbons, such as polyolefins, for example polyethylene which can be crosslinked, polypropylene, polyisobutylene, polymethylbutene-1, polymethylpentene-1, polybutene-1, polyisoprene, polybutadiene, polystyrene, polyisobutylene, copolymers of the monomers based on the above homopolymers, such as ethylene-propylene copolymers, propylene-butene-1 copolymers, propylene-isobutylene copolymers, styrene-butadiene copolymers, and terpolymers of ethylene and propylene with a diene, for example hexadiene, dicyclopentadiene or ethylidene-norbonene; mixtures of the above homopolymers, for example mixtures of polypropylene and polyethylene, polypropylene and polybutene-1, propylene and polyisobutylene.

2. Vinyl polymers which contain halogen, such as polyvinyl chloride, polyvinylidene chloride, polyvinyl fluoride, polychloropropene and chlorinated rubbers.

3. Polymers which are derived from α,β-unsaturated acids and their derivatives, such as polyacrylates and polymethacrylates, polyacrylic amides and polyacrylonitrile, as well as their copolymers with other vinyl compounds, such as acrylonitrile/butadiene/styrene, acrylonitrile/styrene and acrylonitrile/styrene/acrylic ester copolymers.

4. Polymers which are derived from unsaturated alcohols and amines and their acyl derivatives or acetals, such as polyvinyl alcohol, polyvinyl acetate, stearate, benzoate and maleate, polyvinylbutyral, polyallyl phthalate, polyallyl melamine and their copolymers with other vinyl compounds, such as ethylene/vinyl acetate copolymers.

5. Homo- and copolymers which are derived from epoxides, such as polyethylene oxide or the polymers which are derived from bisglycidyl ethers.

6. Polyacetyls, such as polyoxymethylene and polyoxyethylene, and those which contain ethylene oxide as comonomer.

7. Polyphenylene oxides.

8. Polyurethanes and polyureas.
9. Polycarbonates.
10. Polysulphones.
11. Polyamides and copolyamides which are derived from diamines and dicarboxylic acids and/or from aminocarboxylic acids or the corresponding lactames, such as polyamides 6, polyamide 6/6, polyamide 6/10, polyamide 11, polyamide 12.
12. Polyesters which are derived from dicarboxylic acids and dialcohols and/or from hydroxycarboxylic acids or the corresponding lactones, such as polyethylene glycol terephthalate, poly-1,4-dimethylol-cyclohexane terephthalate.
13. Crosslinked polymers which are derived from aldehydes on the one hand and from phenols, ureas and melamines on the other, such as phenol-formaldehyde, urea-formaldehyde and melamine-formaldehyde resins.
14. Alkyd resins, such as glycerol-phthalic acid resins and their mixtures with melamine-formaldehyde resins.
15. Unsaturated polyester resins, which are derived from copolyesters of unsaturated and unsaturated dicarboxylic acids with polyvalent alcohols, as well as vinyl compounds as crosslinking agents, and also their flame-resistant modifications which contain halogen.
16. Natural polymers, such as cellulose, rubber, and their chemically modified homologous compounds, such as cellulose acetate, propionate and butyrates, or the cellulose ethers, such as methyl cellulose.
17. Natural and synthetic organic substances which constitute pure monomeric compounds or mixtures thereof, for example mineral oils, animal and vegetable fats, oils and waxes, or oils, waxes and fats derived from synthetic esters, as well as mixtures of synthetic esters with mineral oils in any desired weight ratios.

The compounds of formula I are incorporated into the substrates in a concentration of 0.005 to 5 percent by weight, referred to the material to be stabilised.

Preferably 0.05 to 1.0%, most preferably 0.1 to 1.0%, by weight of the compounds, referred to the material to be stabilised, is incorporated thereinto. The incorporation may take place before, during, or after the polymerisation, for example by blending in at least one of the compounds of the formula I and optionally further additives by methods which are conventionally used in the art, before or during the moulding, or also by applying the dissolved or dispersed compounds to the polymer, optionally with subsequent evaporation of the solvent.

In the case of crosslinked polyethylene, the compounds are added before the crosslinking.

The compounds of formula I can also be added before or during the polymerisation, whereby stabilised substrates in which the stabilisers are non-volatile or non-extractable can be obtained by a possible incorporation into the polymer chain.

As examples of further additives together with which the stabilisers can be used there may be mentioned: antioxidants, light stability agents, metal deactivators, phosphites, compounds which decompose peroxide, polyamide stabilisers, basic costabilisers, PVC stabilisers, nucleinating agents and urea derivatives, which are described in German Offenlegungsschrift No. 2,427,853, pages 15 to 25. Further possible additives are plasticisers, lubricants, emulsifiers, fillers, such as carbon black, asbestos, kaolin, talcum glass fibres, pigments, fluorescent brighteners, flameproofing agents, antistatic agents.

The following Examples describe the manufacture and use of the compounds according to the invention in more detail, the parts and percentages therein being by weight.

A. Manufacturing Examples

EXAMPLE 1

3-chloro-5-tert. butyl-4-hydroxybenzylophosphonic acid diethyl ester 71.2 g of 3,5-di-tert. butyl-4-hydroxybenzyl-phosphonic acid diethyl ester are dissolved in 200 ml of carbon tetrachloride. After addition of a few drops of pyridine, 40.5 g of sulphuryl chloride are added dropwise, with stirring, at about 0° C in the course of 45 minutes. The reaction mixture is then further stirred for 10 hours at room temperature, in the course of which the formation of sulphur dioxide is observed. After the reaction is terminated, the solvent is removed as far as possible completely in vacuo. The semi-crystalline residue is digested with water and washed neutral and finally recrystallised from aqueous isopropanol in order to purify it. Instead of isopropanol it is also possible to use ethylene glycol monomethyl ether. Toluene is also suitable for effecting recrystallisation, but the crude product must in this case be freed from water beforehand. The 3-chloro-5-tert. butyl-4-hydroxybenzyl-phosphonic acid diethyl ester is obtained in the form of colourless crystals (stabiliser 1) with a melting point of 116° C.

EXAMPLE 2

3-chloro-5-tert. butyl-4-hydroxybenzylphosphonic acid dimethyl ester

The procedure of Example 1 is repeated substituting the corresponding dimethyl ester for the diethyl ester of 3,5-di-tert. butyl-4-hydroxybenzylphosphonic acid, to yield 3-chloro-5-tert. butyl-4-hydroxybenzyl-phosphonic acid dimethyl ester (stabiliser 2) with a melting point of 107° C.

EXAMPLE 3

3-chloro-5-tert. butyl-4-hydroxybenzyl-phosphonic acid di-n-octadecyl ester 80.5 g of 3,5-di-tert. butyl-4-hydroxybenzyl-phosphonic acid di-n-octadecyl ester are dissolved in 250 ml of carbon tetrachloride and the solution is treated briefly with hydrogen chloride gas. The chlorination is effected by carefully bubbling in 10.5 g of chlorine gas for 3 hours at −5° C. The reaction mixture is allowed to come to room temperature and after stirring for a further 3 hours the solvent is removed in vacuo. The oily residue is digested with acetonitrile to purify the reaction product and the cyrstalline precipitate is isolated. The product is further purified by recrystallisation from aqueous ethylene glycol monomethyl ether. The resultant 3-chloro-5-tert. butyl-4-hydroxybenzyl-phosphonic acid di-n-octadecyl ester (stabiliser 3) forms white crystals with a melting point of 55° C.

B. Use Examples

EXAMPLE 4

Stabilising of polypropylene against degradation induced by heat and oxygen during processing The stabilisers listed in Table 1 are mixed homogeneously in a concentration of 0.1% with polypropylene powder of ICI and the mixture is granulated 5 times in succession in a single screw extruder at a maximum temperature of 260° C and 100 rpm. The melt index (MI) of the material is measured after each of the 1st, 2nd and 5th extrusions. (2160 g load at 230° C; g/10 minutes). A degradation of the polymer is expressed in a rapid increase of the melt index.

Stabilisers 1-3 of Examples 1-3 are tested as stabilisers of this invention. 2,6-Di-tert. butyl-4-methylphenol was simultaneously as comparison substance.

The granulates obtained after the 1st, 2nd and 5th extrusions are in addition pressed to 1 mm thick sheets for 10 minutes in a day-light press at 260° C and these are examined visually for their discolouration. Experience shows that pressing the sheet from the granulate does not effect any further discolourations. The values in the Table were obtained by using an empirical colour scale in which 5 denotes colourlessness, 4 a just perceptible slight discolouration and 3 a distinctly perceptible discolouration.

TABLE 1

| Stabiliser Nr. | MI/2160 g at 230° C in g/10 min. after extrusion: | | | Colour rating of the sheets after extrusion: | | | |
|---|---|---|---|---|---|---|---|
| | 1. | 3. | 5. | 1. | 3. | 5. | |
| 1 | 5.7 | 6.2 | 6.9 | 5 | 5 | 5 | products of the invention |
| 2 | 4.4 | 6.3 | 8.9 | 5 | 5 | 5 | |
| 3 | 4.5 | 5.6 | 7.6 | 5 | 5 | 5 | |
| 4 | 5.2 | 6.4 | 7.8 | 3 | 3 | 3 | Comparison product |

I claim:
1. A phosphonate of the general formula I

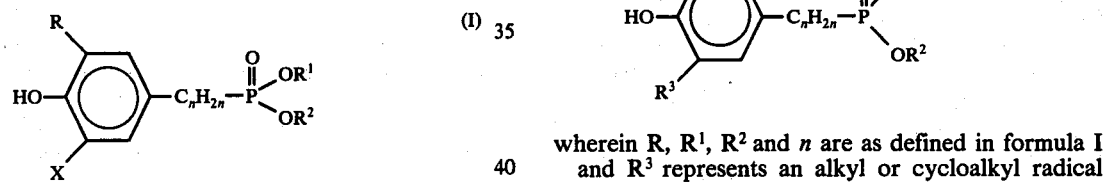

wherein
X represents chlorine,
R represents a linear or branched alkyl radical of 1 to 18 carbon atoms, a cycloalkyl radical of 5 to 8 carbon atoms or an aralkyl radical of 7 to 9 carbon atoms,
$R^1$ represents an alkyl radical of 1 to 22 carbon atoms, a cycloalkyl radical of 5 to 7 carbon atoms, or phenyl or benzyl which is unsubstituted or substituted by alkyl,
$R^2$ independently has the same meaning as $R^1$ or represents a hydrogen atom, and
n is 0, or 1, 2 or 3.

2. A phosphonate of the formula I according to claim 1, wherein R represents an alkyl radical of 1 to 8 carbon atoms.

3. A phosphonate of the formula I according to claim 1, wherein the alkyl radical R is branched at the α-carbon atom.

4. A phosphonate of the formula I according to claim 1, wherein n is 0 or 1.

5. A phosphonate of the formula I according to claim 1, wherein $R^1$ and $R^2$ represent an alkyl radical of 1 to 18 carbon atoms.

6. A phosphonate of the formula I according to claim 1, wherein the radical $R^1$ is the same as the radical $R^2$.

7. A phosphonate of the formula I according to claim 1, wherein R represents an isopropyl or a tert.butyl group, n is 1 and $R^1$ and $R^2$ represent an alkyl radical of 1 to 18 carbon atoms.

8. Phosphonates of the formula I according to claim 7, wherein $R^1$ and $R^2$ represent a methyl, ethyl or octadecyl radical.

9. A phosphonate of claim 4 wherein n is 1.

10. A process for the manufacture of phosphonates of the formula I

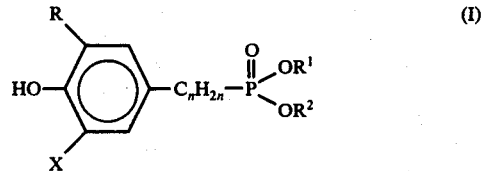

wherein
X represents chlorine,
R represents a linear or branched alkyl radical of 1 to 18 carbon atoms, a cycloalkyl radical of 5 to 8 carbon atoms or an aralkyl radical of 7 to 9 carbon atoms,
$R^1$ represents an alkyl radical of 1 to 22 carbon atoms, a cycloalkyl radical of 5 to 7 carbon atoms, or phenyl or benzyl which is unsubstituted or substituted by alkyl,
$R^2$ independently has the same meaning as $R^1$ or represents a hydrogen atom, and
n is 0, or 1, 2 or 3,
which process comprises reacting a phosphonate of the formula II

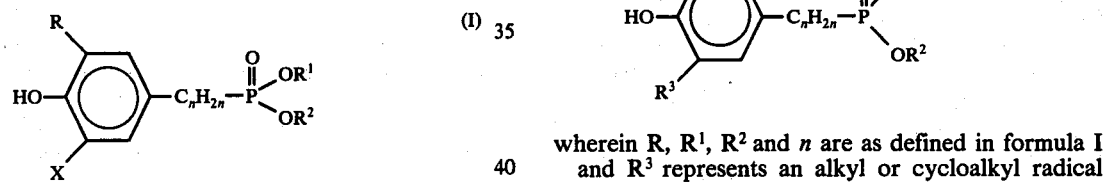

wherein R, $R^1$, $R^2$ and n are as defined in formula I and $R^3$ represents an alkyl or cycloalkyl radical containing a tertiary α-carbon atom, in the presence of an inert solvent and optionally of a basic nitrogen compound, with chlorine or a chlorinating agent, and optionally subsequently hydrolysing the resultant diester to give the monoester.

11. A process according to claim 10, wherein $R^3$ represents an alkyl radical of 4 to 8 carbon atoms.

12. A process according to claim 10, wherein $R^3$ represents a tert. butyl, tert. octyl or α-methylcyclohexyl radical.

13. A process according to claim 10, wherein the reaction is carried out in the presence of a hydrocarbon or halogenated hydrocarbon as solvent.

14. A process according to claim 10, wherein the reaction is carried out at temperatures of −20° to +30° C.

15. A process according to claim 10, wherein at least 1.5 moles of chlorine or of a chlorinating agent are added per mole of a phosphonate of the formula II.

16. A process according to claim 10 wherein the chlorinating agent is sulphuryl chloride.

17. A mixture consisting of an organic material which is sensitive to degradation induced by heat and oxygen and of 0.005 to 5 percent by weight of a phosphonate of the formula I according to claim 1.

18. A mixture according to claim 17, wherein the organic material is a polyolefin.

19. A mixture according to claim 18, wherein the polyolefin is polypropylene.

* * * * *